United States Patent [19]
Barabas et al.

[11] Patent Number: 5,919,796
[45] Date of Patent: Jul. 6, 1999

[54] HYDROXIMIC ACID DERIVATIVES, PHARMACEUTICAL COMPOSITIONS CONTAINING THEM, AND PROCESSES FOR PREPARING THE SAME

[75] Inventors: Mihály Barabas; Ede Marvanyos; László Ürögdi; László Vereczkey; László Jaszlits; Katalin Biró, all of Budapest; Andrea Jednakovits, Szentendre; Erzsébet Radvanyi née Hegedüs; Istvánné Udvardy-Nagy, both of Budapest, all of Hungary

[73] Assignee: BIOREX Kutato es Fejleszto Rt., Hungary

[21] Appl. No.: 08/737,168

[22] PCT Filed: May 4, 1995

[86] PCT No.: PCT/HU95/00014

§ 371 Date: Nov. 5, 1996

§ 102(e) Date: Nov. 5, 1996

[87] PCT Pub. No.: WO95/30649

PCT Pub. Date: Nov. 16, 1995

[30] Foreign Application Priority Data

May 6, 1994 [HU] Hungary ................................ 9401488

[51] Int. Cl.$^6$ .................... A61K 31/44; A61K 31/445; C07D 211/34; C07D 401/12
[52] U.S. Cl. .................. 514/318; 514/238.2; 514/237.2; 514/255; 514/331; 544/124; 544/162; 544/360; 544/398; 546/193; 546/232; 546/338; 564/256
[58] Field of Search ..................................... 546/208, 232, 546/193, 338; 514/318; 544/124, 162, 360, 398; 564/256

[56] References Cited

U.S. PATENT DOCUMENTS 4,451,286 5/1984 Martin ........................................ 71/107

FOREIGN PATENT DOCUMENTS 0 417 210 B1 3/1991 European Pat. Off. .

OTHER PUBLICATIONS

Form PCT/ISA/210 for PCT/HU95/00014, (1995).
Insecticidal (hydroxyimino)butanons, 23–Aliphatics, 102:220443m (1985).
Preparation and Spectral Study of )–methyl=benzamidoximes, Beltrao et al., Chemical Abstracts, 89:215038s (1978).
Tesfamariam, et al., "Contraction of Diabetic Rabbit Aorta Caused by Endothelium–Derived PGH$_2$TxA$_2$," *American Journal of Physiology*, vol. 257, No. 5, 1989, pp. 1327–1333.
Winslow, et al., "Comparative Effects of the Isomers of Bepridil on Isolated Coronary and Aortic Arteries," *European Journal of Pharmacology*, vol. 166, No. 2, (1989), pp. 241–249.
Stanley, "Sensory and Motor Nerve Conduction Velocities and the Latency of the H Reflex During Growth of the Rat," *Experimental Neurology*, vol. 71, No. 2 (1981), pp. 497–506.
DeKonong, et al., "Org. 2766 Improves Functional and Electrophysiological Aspects of Regenerating Sciatic Nerve in the rat," *Peptides*, vol. 8, No. 3 (1987), pp. 415–422.
Morrison, et al., *Organic Chemistry*, Allyn and Bacon, Inc. (Boston), 1983, pp. 205–211.

Primary Examiner—Richard L. Raymond
Attorney, Agent, or Firm—Finnegan, Henderson, Farabow, Garrett & Dunner, L.L.P.

[57] ABSTRACT

Hydroximic acid derivatives possess anti-ischemic effects, and therefore, they are useful for treating ischemic states and diseases, such as myocardial ischemia (which may be induced by occlusion of coronary arteries). These derivatives include compounds of formula (I):

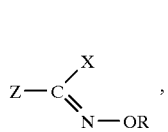

(I)

wherein: X represents a halogen; Z represents an aromatic group, a pyridinyl group, a picolyl group, or a lutidyl group; and R represents an —A—N(R$_1$)R$_2$ group, wherein:

R$_1$ and R$_2$ represent, independently from each other, hydrogen or an alkyl group;

or R$_1$ and R$_2$, together with the adjacent nitrogen atom, form a 5- to 7-membered, saturated heterocyclic group optionally containing an additional nitrogen, oxygen, or sulfur atom, the heterocyclic group optionally being substituted by at least one alkyl group; and A represents a straight or branched chain alkylene group, as well as pharmaceutically acceptable acid addition salts thereof. The invention further relates to processes for preparing the above noted compounds, and pharmaceutical compositions containing these compounds or their pharmaceutically acceptable acid addition salts as an active ingredient. Additionally, the invention relates to intermediate compounds of formula II used in preparing the compounds of formula I. Formula II is as follows:

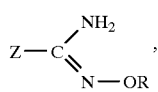

(II)

In formula II, the variables Z and R have the same definitions provided above.

21 Claims, No Drawings

HYDROXIMIC ACID DERIVATIVES, PHARMACEUTICAL COMPOSITIONS CONTAINING THEM, AND PROCESSES FOR PREPARING THE SAME

The present application is a 371 of PCT/HU95/00014, filed May 4, 1995.

The invention relates to novel, biologically active hydroximic acid derivatives of the formula

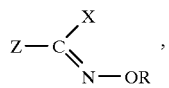

(I)

wherein

X means halogen;

Z stands for an aromatic group, pyridinyl group or the like; and

R represents an alkyl or phenylalkyl group or an —A—N(R$_1$)R$_2$ group, and in the latter R$_1$ and R$_2$ stand, independently from each other, for hydrogen an alkyl group; or R$_1$ and R$_2$, together with the adjacent nitrogen atom, form a 5- to 7-membered, saturated heterocyclic group optionally containing an additional nitrogen, oxygen or sulfur atom, the heterocyclic group optionally being substituted by at least one alkyl group; and A stands for a straight or branched chain alkylene group, as well as their pharmaceutically acceptable acid addition salts and pharmaceutical compositions containing these compounds. Furthermore, the invention relates to a process for the preparation of the above compounds and to a method for the treatment of ischemic states or diseases in mammals, including men.

X as halogen means fluorine, chlorine, bromine or iodine; compounds containing chlorine as X are preferred.

Z as an aromatic group is preferably a phenyl, phenylalkyl, substituted phenyl, substituted phenylalkyl or naphthyl group. The phenyl group of the above substituted groups may be substituted by 1 to 3 identical or different group(s), which is (are) suitably halogen, haloalkyl, alkyl, hydroxy, alkoxy, nitro, amino, mono- or dialkylamino groups.

The term "Z stands for a pyridinyl group or the like" means a pyridinyl group or its homologues, e.g. picolyl or lutidyl group. Pyridinyl group is particularly preferable; whereas 3-pyridinyl group proved to be most advantageous.

Above and in the forthcoming, alkyl or alkoxy groups as R, R$_1$ and R$_2$ or as substituents contain preferably 1 to 8, suitably 1 to 6, most preferably 1 to 4 carbon atoms unless stated otherwise. Methyl, ethyl or n-propyl groups are most preferred.

Thus, the phenylalkyl group is in most cases a benzyl or phenylethyl group; whereas the mono- and dialkylamino groups are preferably monoC$_{1-4}$alkyl or diC$_{1-4}$alkyl groups, respectively.

The haloalkyl group may contain one or more above-mentioned halogen(s) or it may be a perfluoroalkyl group. Preferred are e.g. chloromethyl, 2-chloroethyl or trifluoromethyl groups.

The heterocyclic group formed by R$_1$, R$_2$ and the adjacent nitrogen together is preferably a piperidino, piperazino or morpholino group. These groups may optionally be substituted by at least one alkyl group defined above. Thus, these groups may be e.g. a 4-methylpiperazinyl or 2,2-dimethylpiperidinyl group.

The alkylene group A may contain a straight or branched chain, and suitably it contains 1 to 8, preferably 1 to 5 carbon atoms. The 1,2-ethylene, 1,3-propylene and 1,4-butylene groups are especially advantageous.

All compounds of formula (I) are novel. A part of the starting materials for their preparation is known whereas others are new. The methods of preparation of the new starting materials are described in the corresponding examples.

Insecticides being structurally similar to compounds of the formula (I) are disclosed in the Japanese patent application published under No. 60.0008253 (Kokai), and β-blocking agents being structurally similar to the compounds of formula (I) are claimed in the European patent specification No. 0,147,210.

Structurally, compounds disclosed in the latter document differ from the compounds of formula (I) in that a —CH$_2$—CH(OH)—CH$_2$—(2-hydroxy-propylene) moiety is present between the terminal —NR$^1$R$^2$ group and the remaining part of the molecule instead of the unsubstituted straight or branched alkylene group symbolized by A in the compounds of the formula (I). The compounds described in the European patent specification 0,417,210 are diabetes selective β-antagonists and can be used especially in the therapy of diabetic angiopathy.

Beltrao, T. M. et al describe the preparative and spectroscopic investigation of O-metbylbenzamidoximes of the formula p-R$^1$—C$_6$H$_4$—C(NH$_2$)—NOR (R=Me, R$^1$=H, Me, Cl, Br, NO$_2$) in their article "Preparation and spectral study of O-methylbenzamidoximes" [An. Acad. Bras. Cienc.1978, (50)2,159–64]. The synthetic route described is traditional, starting with addition of hydroxylamine to a substituted benzonitrile, followed by O-methylation with Me$_2$SO$_4$. Beside the investigation of the tautomerism of the products in solution by IR spectroscopy it is also described that some of the O-methylbenzamidoximes was found to be active against *Trypanosoma cruzi.*

The structurally closest analogues of compounds of formula (I) from the prior art are the classical β-adrenerg receptor antagonists, more specifically the family of the β-blocker aryloxypropanolamine derivatives. These compounds always possess a secondary hydroxyl group in their alkylene moieties binding the terminal —NR$^1$R$^2$ group to the molecule, and the SAR studies have clearly demonstrated that this substructure is essential for their biological activity [see in this respect e.g. Comprehensive Medicinal Chemistry (ed. C. Hansch), Vol. 3. "Membranes and Receptors" (ed. J. C. Emmett), Pergamon Press, 1990, pp. 199,200 and 206]. It has to be noted that the presence of this hydroxyl group introduces chirality to the structure of these compounds.

However, it is always desirable that compounds for medicinal use have the simplest possible structure that makes their preparation and biological investigation easy. Recently researchers have been seeking particularly for molecules without chirality in order to avoid the laborious and expensive investigation of the stereoisomeric forms and their mixtures, required more and more by the registration authorities in the last few years. However, based of the similarities between both the chemical structures and the biological effect of the above mentioned β-blockers and the compounds described in the cited EP 0,417,210 patent specification, it could be expected that omitting the hydroxyl group from latter derivatives should result in loss of their biological activity as well.

Surprisingly, we have found that compounds of formula (I) i.e. hydroximic acid derivatives having an aminoalkyl portion that contains no hydroxyl functionality, possess therapeutically valuable biological activity, consequently, they are useful as active ingredients in medicaments. Based on this recognition the invention provides biologically active chemical substances that can be prepared and biologically assessed without the difficulties typically arising at the closely related optically active compounds.

The compounds of the formula (I) can be prepared by using several known processes from which the following ones will be described without intending any* limitation as to the scope claimed.

a) A compound of the formula

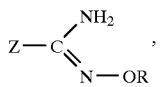

(II)

wherein Z and R are as defined form formula (I), or an acid addition salt thereof is treated with a diazotizing agent known per se in the presence of a hydrogen halide.

Alkali metal nitrites (e. g. sodium or potassium nitrite) or an alkyl nitrrie (e.g. isoamyl nitrite or tert-butyl nitrite) are useful diazotizing agents in the presence of a hydrogen halide (e.g. hydrochloric acid, hydrogen bromide or the like). After carrying out the reaction at a temperature between −5° C. and 15° C., the mixture is stirred until decomposition of the transitorily formed diazonium salt, preferably for 10 to 60 minutes.

b) A compound of the formula

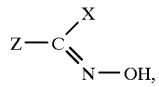

(III)

wherein X and Z are as defined for formula (I), is reacted with a compound of the formula

R—Y,    (IV)

wherein R is as defined above and Y means a leaving group. This reaction is carried out at room temperature in the presence of an acid binding agent.

c) A compound of formula

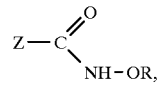

(V)

or formula

Z—CH=NOR,    (VI)

respectively, wherein Z and R are as defined above, is treated with a suitable halogenating agent.

For halogenation of the compounds of formula (V), e.g. thionyl chloride, phosphorus pentahalides, phosphorus oxyhalides, phosgene, carbon tetrachloride/triphenylphosphine, hydrogen fluoride/pyridine, diethylamino-sulfur-trifluoride and the like are useful. The reaction is carried out at an elevated temperature, suitably at the boiling point of the reaction mixture.

For halogenation of the compounds of formula (VI), elemental halogens (e.g. chlorine or bromine) hypohalogenites (e.g. sodium hypohalogenite, tertbutyl hypohalogenite) or N-chlorosuccinimide, N-bromosuccinime and the like are useful. The reaction is carried out in the presence of an organic solvent, e.g. chloroform or benzene, suitably at room temperature.

d) Alternatively, if it is desired to prepare a compound containing an —A—N($R_1$)$R_2$ group as R, belonging therefore to a narrower group of the compounds of formula (I), an amine of the formula HN($R_1$)$R_2$, wherein $R_1$ and $R_2$ are as defined for formula (I), is reacted with a compound of formula

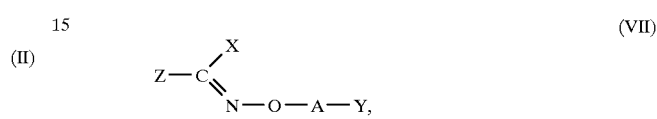

(VII)

wherein Z, X, Y and A are as defined above. This reaction is performed in an organic solvent.

If desired, the compounds of the formula (I) prepared by using any processes a), b), c) or d), respectively, can be converted to pharmaceutically acceptable acid addition salts in a manner known per se.

During our investigations on the compounds prepared, it has been found that they possess anti-ischemic effect.

The Reperfusion-induced arrhythmia [ventricular tachycardia (VI) and ventricular fibrillation (VF)] was studied on anaesthetized rats. Myocardial ischemia was elicited by compressing the left-sided descending coronary artery for 5 minutes and after the ceasing thereof, by a 10-minute reperfusion of the heart. ECG was continuously monitored, and the change of the mean duration of VT and VF under effect of the test compounds, as well as the survival, were measured in the first 3 minutes of reperfusion. The test compounds were administered in an intravenous (i.v.) dose of 1 mg/kg by 5 minutes before compressing the left-sided descending coronary artery. The survival of experimental animals was found to be 100% by using e.g. the compounds of Examples 2 and 7.

The vasorelaxant effect of the compounds was investigated in vitro on the thoracal aorta isolated from rabbit [Am. J. Physiol. 257, 1327–1333 (1989)]. Our results are summarized in Table 1.

TABLE 1

| Compound No. | 2 | 4 | 5 | 6 | 7 | 8 | 9 | Ref |
|---|---|---|---|---|---|---|---|---|
| $EC_{50}$ (× $10^{-5}$ M) | 2.7 | 8.2 | 2.4 | 1.3 | 0.6 | 1.5 | 7.6 | 8.3 |

Reference drug: Bepridil [Eur. J. Pharm. 166, 241–249 (1989)].

The compound number given above is the of the corresponding Example in the present patent application.

Furthermore, the effect of the compounds of the invention in the treatment of complications associated with the diabetic angiopathy was studied. The in vivo action was measured on rats, by the change of rate of the impulse conduction in an STZ-induced diabetic state as follows.

The rate of motor and sensory impulse conduction (MCR or SCR, respectively) of the sciatic and tibial nerve, respectively, as mixed type nerves was determined by using the method of E. F. Stenley [Experimental Neurology 71, 497–506 (1981) as modified by P. De Koning and W. H. Gispen: Peptides 8, 415–412 (1987)]. The electrophysiological measurements were carried out on anaesthetized male Cr:Wistar rats at the end of a one-month period of treatment with 20 mg/kg administered orally (p.o.). The sciatic or tibial nerve, respectively, was excited by needle electrodes stitched near the nerve on the lower extremity and the electromyographic (EMG) responses of the plantar muscle were registered. Five EMG-s each were averaged and the results were stored in a computer. The latency periods of the motor and sensory components were measured. The rates of impulse conduction were calculated from the ratio of the distance between two sites of excitation to the differences of latency.

The reduced impulse conduction of the diabetic animals was restored by the compounds investigated in the following percentage values:

| Compound No.    | MCR correction (%) | SCR correction (%) |
|-----------------|--------------------|--------------------|
| 2               | 100                | 100                |
| 7               | 48                 | 64                 |
| Reference drug* | 40                 | 45                 |

*50 mg/kg of aminoguanidine

The active compounds of the invention can be administered mainly by oral or parenteral route, e.g. in a daily dose of 1–10 mg/kg body weight to an adult human.

For the preparation of oral compositions e.g. lactose or starch may be used as filling material. Gelatine, (carboxymethyl)cellulose sodium, methyl cellulose, polyvinylpyrrolidine or starch gum are useful binding or granulating agents. Potato starch or microcrystalline cellulose are mainly added as disintegrating agents though ultraamylopectin, formaldehyde-casein and the like are also suitable. Useful anti-adhesive and sliding materials are talc, colloidal silicic acid, stearin, calcium or magnesium stearate or the like.

Tablets can be prepared e.g. by wet granulation and subsequent compression. After mixing the active components and excipients as well as optionally a part of the disintegrating additive, they are granulated together with the aqueous, alcoholic or aqueous-alcoholic solution of the binding agent in suitable equipment, and then the granular substance is dried. Thereafter, the other disintegrating, sliding and antiadhesive auxiliaries are mixed to the dried granulate and the mixture is compressed to tablets. Optionally the tablet is provided with a groove for facilitating the administration. Tablets can directly be prepared also by compression from a mixture of the active ingredient and suitable auxiliaries. If desired, the tablets may be converted to dragées by using additives commonly employed for the preparation of medicaments such as stabilizing, savouring agents and dyes, e.g. sugar, cellulose derivatives [methyl- or ethylcellulose, (carboxymethyl)cellulose sodium and the like], polyvinylpyrrolidone, calcium phosphate, calcium carbonate, food dyes, food dye lacquers, aromatizing agents, iron oxide pigments and the like.

For the preparation of capsules, a mixture containing the active ingredient(s) and auxiliaries is filled into capsules.

For parenteral administration, the composition is formulated to an injectable solution. For preparing such a solution, the active ingredients are dissolved in distilled water and/or various organic solvents, e.g. glycol ethers, optionally in the presence of solubilizing agents such as polyoxyethylene sorbitan monolaurate, monooleate or monostearate (Tween 20, Tween 60 or Tween 80, respectively). In addition, the injectable solution may contain various auxiliaries, e.g. preserving agents such as benzyl alcohol, methyl or propyl p-hydroxybenzoate, benzalkonium chloride or phenyl mercury borate and the like; as well as antioxidants, e.g. ascorbic acid, tocopherol, sodium pyrosulfate and optionally complex-forming substances such as ethylenediamine tetraacetate for binding metal traces; furthermore, pH-adjusting agents and buffers, as well as optionally, a local anaesthetic such as lidocaine, can be included. Before filling the injectable solution containing the composition of the invention into the ampoule, the solution is filtered, and after filling in, it is sterilized.

The invention also relates to a method for the treatment of ischemic states or diseases. This method comprises administering a therapeutically effective amount of an active compound of formula (I) or a pharmaceutically acceptable acid addition salt thereof to the patient.

The invention relates also to certain novel intermediates of formula (II), from which the following ones are preferred:
N-(3-piperidino- 1-propoxy)-3-pyridinecarboxamidine,
N-methoxy-3-pyridinecarboxamidine,
N-(3-morpholinopropoxy)-3-pyridinecarboxamidine,
N-(2-piperidinoethoxy)-3-pyridinecarboxamidine,
N-[3-(1-piperidinyl)-propoxy]-3'-(trifluoromethyl) benzamidine,
N-[3-(4-methylpiperazin-1-yl)1-propoxy]-3-pyridinecarboxamidine,
N-(2,2-dimethyl-3-piperidinopropoxy)-3-pyridinecarboxamidine and acid addition salts of these compounds.

The invention is illustrated in more detail by the following non-limiting Examples.

EXAMPLE 1

Preparation of N-benzyloxy-3-pyridinecarboximidoyl chloride hydrochloride

A) A solution containing 6.38 g (26.7 mmoles) of N-benzyloxy-3-pyridinecarboxamidine hydrochloride in a mixture of 27.4 ml of concentrated hydrochloric acid and 73 ml of water is cooled to 5° C., and 2.29 g (33.2 mmoles) of sodium nitrite dissolved in 13 ml of water are dropwise added. The mixture is stirred at this temperature an additional 30 minutes. After layering 50 ml of chloroform to the mixture, it is alkalinized to pH 8 to 9 by adding solid sodium carbonate. After separation of the chloroformic phase, the aqueous phase is again extracted twice with 50 ml of chloroform each, then the combined chloroformic solution is washed with 10 ml of saturated saline solution, dried over anhydrous sodium sulfate and evaporated.

The residue obtained (5.49 g, 79%) is dissolved in 55 ml of isopropanol, and 10 ml of a 2.1 molar solution of hydrogen chloride in isopropanol are added to obtain the hydrochloride salt of the product in a yield of 3.88 g (51%), m.p.: 146–151.5 ° C. (recrystallized from methanol/ether).

$^1$H-NMR (DMSO): 9.1–8.8 (broad, 1H, NH$^+$), 9.07 (d, 1H), 8.90 (dd, 1H), 8.56 (m, 1H), 7.9 (dd, 1H pyridine 2-6-4-5), 7.5–7.3 (m, 5H Ph), 5.38 (s, 2H CH$_2$) ppm. $^{13}$C-NMR (DMSO):146.4, 142.3, 139.2, 129.8, 125.8 (pyridine 2-6-4-3-5), 133.0 [C(Cl)=NO], 135.9, 128.5, 128.3, 128.2 (Ph), 77.3 (CH$_2$) ppm. Elementar analysis for C$_{13}$H$_{11}$NOCl.HCl: calculated: C 55.1; H 4.3; N 9.9; Cl 25.0%; found: C 55.0; H 4.2; N 10.1; Cl 25.2%.

B) 2.38 g (10 mmoles) of N-(benzyloxy)nicotinamide (Beilstein 22/V, page 120) are boiled under reflux in 20 ml of thionyl chloride for 2 hours. After distilling off the excess thionyl chloride, the residue is crystallized from isopropanol to give 1.75 g (62%) of the desired product, the physical characteristics of which are identical to those of the product prepared by method A).

EXAMPLE 2

Preparation of N-(3-piperidinopropoxy)-3-pyridinecarboximodyl chloride dihydrochloride A) After cooling to 0° C. a mixture of 10 ml of distilled water and 4.36 ml of concentrated hydrochloric acid, 2 g (7.62 mmoles) of N-(3-piperidino-1-propoxy)-3-pyridinecarboxamidine are added under stirring. To the yellow solution 2.7 g (3.81 mmoles) of sodium nitrite dissolved in 10 ml of water are added dropwise at −5° C. during 30 minutes. After stirring the greenish solution at −5° C. for 1.5 hours, the pH of the solution is adjusted to 10 by adding 1N aqueous sodium hydroxide solution under cooling, then the solution is extracted 3 times with 40 ml of chloroform. The organic phase is washed with 20 ml of water, dried over sodium sulfate and evaporated. The residue is purified by column chromatography (Merck Kieselgel 60; eluent: chloroform/methanol 1:1) to obtain 1.7 g (79.2%) of the base corresponding to the title compound.

The title hydrochloride is prepared from the base obtained by adding an ethanolic solution of hydrogen chloride, m.p.: 165–167° C.

IR (KBr) γ cm$^{-1}$: 3015, 2945, 2617, 2515, 2088, 1982, 1600, 1570, 1437, 1402, 1200, 1060, 988, 912, 808. $^1$H-NMR (DMSO-d$_6$): 9.0 (dd, 1H, Ar-H), 8.8 (dd, 1H, Ar-H), 8.3 (dd, 1H, Ar-H), 7.7 (ddd, 1H, Ar-H), 4.41 (t, 2H, —OCH$_2$), 3.41–1.37 (m, 12H), 1.8 (quintet, 2H, —OCH$_2$CH$_2$CH) ppm. $^{13}$C-NMR (DMSO-d$_6$): 148.5 (d, Ar), 144.7 (d, Ar), 136.4 (d, Ar), 133.5 (s, C-Cl), 128.6 (s, Ar), 124.2 (d, Ar), 72.5 (t, OCH$_2$), 52.4 (t, CH$_2$—N), 51.4 (t, N—CH$_2$—CH$_2$—CH$_2$—CH$_2$—CH$_2$), 22.6 (t, 0—CH$_2$—CH$_2$—CH$_2$), 21.6 (t, N—CH$_2$—CH$_2$—CH$_2$—CH$_2$), 20.8 (t, N—CH$_2$—CH$_2$—CH$_2$—CH$_2$—CH$_2$) ppm.

The above starting material can be prepared as follows:

After dissolving 2.86 g (51.06 mmoles) of potassium hydroxide in 20 ml of abs. ethanol, 6.45 g (47.0 mmoles) of 3-pyridinecarboxamide oxime are portionwise added while stirring. After dissolution, 7.7 g (47.66 mmoles) of 1-(3-chloropropyl)piperidine dissolved in 5 ml of ethanol are dropwise added. After 9-hour reaction, the precipitated potassium chloride is filtered off, the ethanolic solution is clarified by activated carbon and evaporated. After taking up in 100 ml of chloroform, the evaporation residue is washed 3 times with 100 ml of 1N sodium hydroxide solution each, then with 50 ml of water. After separation, the organic phase is dried over sodium sulfate, filtered and evaporated. The oily residue becomes crystalline on cooling. The crystals are triturated with about 20 ml of ether, filtered and dried to give a beige product in a yield of 4.8 g (38.9%).

IR KBr γ cm$^{-1}$: 3422, 3107, 2937, 2870, 2819, 1640, 1479, 1391, 1309, 1194, 1123, 1059, 1042, 982, 916. $^1$H-NMR (DMSO-d$_6$): 8.85 (dd, 1H, J1=1,8 Hz, J2=0.8 Hz, Ar (2) H), 8.58 (dd, 1H, Ar(6)H), 8.01 (dt, 1H, Ar(4)H), 7.40 (ddd, 1H, Ar(5)H), 6.16 (broad, 2H, NH$_2$), 4.00 (t, 2H, J=6.6 Hz, OCH$_2$), 2.43 (m, 2H, overlapped, OCH$_2$CH$_2$N), 2.33 (m, 4H, —N—CH$_2$CH$_2$CH$_2$CH$_2$CH$_2$), 1.77 (quintet, 2H OCH$_2$CH$_2$CH$_2$), 1.48 (m, 4H, —N—CH$_2$CH$_2$CH$_2$CH$_2$), 1.40 (m, 2H, —N—CH$_2$CH$_2$CH$_2$CH$_2$CH$_2$) ppm. $^{13}$C-NMR (DMSO-d$_6$): 149.9 (d, Ar), 149.0 (s, C—NH$_2$), 146.6 (d, Ar), 133.1 (d, Ar), 128.3 (s, Ar), 123.1 (d, Ar), 49.9 (t, OCH$_2$), 55.3 (t, OCH$_2$CH$_2$), 53.9 (t, OCH$_2$CH$_2$CH$_2$—N—CH$_2$), 26.1 (t, OCH$_2$CH$_2$), 25.4 (t, —N—CH$_2$—CH$_2$CH$_2$CH$_2$CH$_2$), 24.0 (t, —N—CH$_2$CH$_2$CH$_2$CH$_2$) ppm.

B) 5.49 g (0.04 moles) of nicotinic acid amidoxime (Beilstein E III/IV 22, page 439) are added under stirring to a solution containing 2.24 g (0.04 moles of potassium hydroxide in 30 ml of ethanol while stirring and, after complete dissolution, 3.93 ml (6.3 g, 0.04 moles) of 1-chloro-3-bromopropane are dropwise added during 15 minutes. After boiling the reaction mixture under reflux for 6 hours and then cooling down, the inorganic salt precipitated is filtered off and the solution is evaporated under reduced pressure. The residue is dissolved in 100 ml of chloroform, washed with 50 ml of 2N sodium hydroxide solution, then 50 ml of water, dried over sodium sulfate and evaporated.

The oily residue is dissolved at −5° C. in a mixture of 80 ml of distilled water and 23 ml of 37% hydrochloric acid. To this solution, 13.79 g (0.2 moles) of sodium nitrite dissolved in 60 ml of water are dropwise added at the same temperature, then the reaction mixture is stirred at −5° C. for additional 2 hours. Subsequently, 150 ml of chloroform and 200 ml of sodium hydroxide solution are added and it is extracted. The organic phase is washed with 50 ml of water, dried over sodium sulfate and evaporated.

The obtained compound of formula (VII) [wherein Z=3-pyridinyl, Y=X=Cl and A=(CH$_2$)$_3$] is dissolved in 100 ml of benzene, cooled to −10° C. and 7.91 ml (6.81 g, 0.08 moles) of piperidine are dropwise added under stirring. After boiling the mixture under reflux for 8 hours, then cooling down, the solid piperidine hydrochloride precipitate is filtered off and thoroughly washed with benzene. The filtrate is twice extracted with 200 ml of 3N aqueous hydrochloric acid solution each. The combined aqueous phase is made alkaline up to pH 10 by adding 4N sodium hydroxide solution, then extracted twice with 150 ml of chloroform each. The combined chloroformic phase is dried over sodium sulfate, filtered and evaporated.

The brown oily residue is purified by column chromatography (Merck Kieselgel 60, eluent: chloroform/methanol 1:1) to obtain 4.81 g (42.7%) of base which is converted to the dihydrochloride salt as described in Example 3A.

EXAMPLE 3

Preparation of N-methoxy-3-pyridinecarboximidoyl chloride hydrochloride

A) A solution containing 2.5 g (13.3 mmoles) of N-methoxy-3-pyridinecarboxamidine hydrochloride in mixture of 3.7 ml of concentrated hydrochloric acid and 36 ml of water is cooled to 5° C., then a solution of 1.14 g (16.4 mmoles) of sodium nitrite in 6.5 ml of water is dropwise added and stirred at the same temperature for an additional 30 minutes.

After layering 30 ml of chloroform to the mixture and then adjusting the pH-value to 8–9 by adding solid sodium carbonate, the chloroformic phase is separated, the aqueous layer is again extracted with 30 ml of chloroform, then the combined chloroformic solution is washed with 10 ml of saturated saline solution, dried over sodium sulfate and evaporated.

The obtained residue weighing 1.9 g is dissolved in 10 ml of isopropanol, and 5.2 ml of 2.1 molar solution of hydrogen chloride in isopropanol are added to obtain the hydrochloride salt in title in a yield of 1.06 g (36%), m.p.: 136–139° C. $^1$H-NMR (DMSO): 11.5 (broad, 1H, NH$^+$), 9.06 (d, 1H), 8.91 (dd, 1H), 8.59 (m, 1H), 7.93 (dd, 1H pyridine 2-6-4-5), 4.1 (s, 3H, CH$_3$) ppm. $^{13}$C-NMR (DMSO): 145.7, 142.1, 139,7, 129.8, 126.0 (pyridine 2-6-4-3-5), 132.2 [C(Cl) =NO], 63.5 (CH$_3$) ppm.

The above starting material is prepared as follows:

The mixture containing 6.85 g (0.05 mmoles) of 3-pyridinecarboxamid-oxime, 3.37 g (0.06 moles) of potassium hydroxide, 3.15 ml (7.18 g, 0.051 moles) of methyl iodide and 100 ml of ethanol is stirred at room temperature for 3 hours. After evaporation, the residue is dissolved in 100 ml of water, extracted 3 times with 100 ml of ethyl acetate each, and the combined organic phase is washed with 100 ml of 1N sodium hydroxide solution, then twice with 50 ml of saturated saline solution each, dried over sodium sulfate and evaporated.

The obtained residue (3.5 g) is dissolved in 50 ml of ether, clarified with activated carbon and again evaporated to obtain 3.14 g (42%) of solid product, m.p.: 49–56° C.

After dissolving the crude product in 30 ml of a isopropanol, 9.8 ml of 2.1 molar solution of hydrogen chloride in isopropanol are added to obtain the hydrochloride, which is then crystallized to give 3.38 g (36%) of the aimed hydrochloride, m.p.: 158–164° C. (recrystallized from methanol/ether).

B) Gaseous chlorine is introduced in a slow flow for 30 minutes to the solution of 2.72 g (20 mmoles) of O-methyl-nicotinealdoxime dissolved in 30 ml of chloroform. After evaporating the mixture to dryness, the residue is recrystallized from isopropanol to give the title hydrochloride in a yield of 2.4 g (58%), the physical characteristics of which are identical to those prepared by method A).

EXAMPLE 4
Preparation of O-(3-diethylaminopropyl)-3-pyridinehydroximoyl chloride hydrochloride 9.5 g (37.9 mmoles) of N-(3-diethylaminopropoxy)-3-pyridinecarboxamidine are added under stirring to the mixture of 65 ml of distilled water and 21.7 ml of concentrated hydrochloric acid, cooled to 0° C. To the yellow solution, 13.08 g (189.5 mmoles) of sodium nitrite dissolved in 54 ml of distilled water are dropwise added at −5° C. during 50 minutes, then the reaction mixture is stirred at a temperature of −5° C. for 2 hours. Subsequently, the pH of the solution is adjusted to 11 by adding 2N sodium hydroxide solution, and the mixture is extracted 3 times with 70 ml of chloroform each. The organic phase is washed with 30 ml of water, dried over sodium sulfate and evaporated. The residue is purified by column chromatography (adsorbent: Merck Kieselgel 60; eluent: chloroform/methanol 1:1). The base obtained in a yield of 5.17 g (50.6%) is transformed by adding methanolic solution of hydrogen chloride to obtain the title hydrochloride, m.p.: 152–153° C.

IR (KBr) $\gamma$ cm$^{-1}$: 3044, 2937, 2752, 2533, 2658, 2492, 1587, 1477, 1416, 1055, 1022, 976, f397, 816, 704. $^1$H-NMR (DMSO-d$_6$): 11.1 (broad, 1H), 9.0 (dd, 1H, Ar-H), 8.7 (dd, 1H, Ar-H J$_1$=5.3 Hz, J$_2$=1.5Hz), 8.18 (dt, 1H, Ar-H, J=8.7 Hz, J$_2$=J$_3$=1.5 Hz (dd, 1H, Ar-H), 4.45 (t, 2H, J=6.2 Hz, OCH$_2$), 3.1 (m, 2H, CH$_2$CH$_2$—N), 3.1 (m, 2H, CH$_2$CH$_2$CH$_3$), 2.2 (m, 2H, OCH$_2$—CH$_2$), 1.23 (t, 3H, J=7.2 Hz, CH$_3$) ppm. $^{13}$C-NM (DMSO-d$_6$): 151.4 (d, Ar), 147.1 (d, Ar), 134.6 (s, C—Cl), 134.4 (d, Ar), 127.2 (s, Ar), 123.6 (d, Ar), 72.2 (t, OCH$_2$), 46.7 (t, CH$_2$N), 45.8 (t, N—CH$_2$—CH$_3$), 22.5 (t, CH$_2$—CH$_2$—CH$_2$), 8.1 (q, CH$_3$) ppm.

EXAMPLE 5
Preparation of O-(3-morpholinopropyl)-3-pyridinehydroximoyl chloride dihydrochloride 2.5 g (9.45 mmoles) of N-(3-morpholinopropoxy)-3-pyridinecarboxamidine are added to the mixture of 15 ml of distilled water and 5.41 ml of concentrated hydrochloric acid cooled to 0° C. under stirring. To the yellow solution, 3.26 g (47.25 mmoles) of sodium nitrite dissolved in 15 ml of water are dropwise added at a temperature of −5° C. during 30 minutes. The reaction mixture is stirred at −5° C. for 2 hours. Then, the pH of the solution is adjusted to 11 by adding 2N sodium hydroxide solution, and it is extracted 3 times with 5 ml of chloroform each. The organic phase is washed with 30 ml of water, dried over sodium sulfate and evaporated. An ethereal solution of hydrogen chloride is added to the evaporation residue until reaching pH of 2 value to obtain 2.42 g (71.8%) of the title dihydrochloride, m.p.: 196–200° C.

IR (KBr) $\gamma$ cm$^{-1}$: 3017, 2483, 2095, 1630, 1574, 1551, 1480, 1350, 1281, 1111, 1083, 980, 808, 714, 675. $^1$H-NMR (DMSO-d$_6$): 11.4 (broad, 1H), 11.15 (broad, 1H), 9.12 (d, 1H, J=1.5 Hz), 8.92 (dd, 1H, J1=5.3 Hz, J2=5.3 Hz) 8.60 (dt, 1H, J=8.7 Hz, J$_2$=J$_3$=1,5 Hz). 7.91 (dd. 1H, J$_1$=8.7 Hz, J$_2$=5.3 Hz), 4.44 (t, 2H, OCH$_2$), 3.9 (m, 4H, N—CH$_2$—CH$_2$—O), 3.44 (d, 2H, J=12.2 Hz, N—CH$_2$—CH$_2$—O, equ), 3.3–3.0 (m, 2H, N—CH$_2$—CH$_2$—O, ax.), 3.3–3.0 (m, 2H, CH$_2$—CH$_2$—N), 2.3 (m, 2H, CH$_2$—CH$_2$—CH$_2$) ppm. $^{13}$C-NMR (DMSO-d$_6$): 146.6 (d, Ar), 143.0 (d, Ar), 139.3 (d, Ar), 133.3 (C—Cl), .129.7 (s, Ar), 125.7 (d, Ar), 72.8 (t, OCH$_2$), 62.9 (t, N—CH$_2$—CH$_2$—O), 52.6 ) (t, CH$_2$—CH$_2$—N), 50.7 (t, N—CH$_2$—CH$_2$—O), 22.6 (t, O—CH$_2$—CH$_2$—CH$_2$—N) ppm. Elementar analysis for C$_{13}$H$_{18}$N$_3$O$_2$.2HCl: calculated: C 43.8; H 5.65; N 11.78%; found: C 44.4; H 5.7; N 11.9%.

The above starting substance is prepared as follows:

To the solution of 5.72 g (0.102 moles) of potassium hydroxide in 40 ml of ethanol, 12.89 g (0.094 moles) of 3-pyridinealdoxime are added under stirring, then, after dissolution, 15.6 g (0.0953 moles) of 1-(3-chloropropyl) morpholine dissolved in 10 ml of ethanol are dropwise added to the reaction mixture, which is boiled under reflux for 9 hours. The precipitated potassium chloride is filtered off, the filtrate is clarified by using activated carbon and evaporated. After dissolution of the residue in 200 ml of chloroform, the solution is washed 3 times with 100 ml of 1N sodium hydroxide solution each, then 3 times with 100 ml of water each. After drying the organic phase over sodium sulfate and filtering, the filtrate is evaporated. The residue is purified by column chromatography (adsorbent: Merck Kieselgel 60; eluent: chloroform/methanol 5:1). The purified base is crystallized from ether to obtain a yield of 3.6 g (14.49%), m.p.: 61–63° C. $^1$H-NMR (DMSO-d$_6$): 8.85 (d, 1H, J=1.5 Hz, Ar), 8.62 (dd, 1H, J$_1$=5.3 Hz, J$_2$=1.5 Hz, Ar), 7.94 (dt, 1H, J=8.7 Hz, J$_2$=J$_3$=1.5 Hz, Ar), 7.31 (dd, 1H, J$_1$=8.7 Hz, J$_2$=5.3 Hz, Ar), 4.96 (broad s, 2H, NH$_2$), 4.16 (t, 2H, J=6.5 Hz, =N—O—CH$_2$), 3.70 (t, 4H, N—CH$_2$—CH$_2$—O), 2.48 (t, 2H, J=6.5 Hz, overlapped, N—O—CH$_2$—CH$_2$—CH$_2$—N), 2.47 (m, 4H, —N—CH$_2$—CH$_2$—O), 1.92 (m, 2H, O—CH$_2$—CH$_2$—CH$_2$—N) ppm. $^{13}$C—NMR (DMSO-d$_6$): 150.7 (d, Ar), 149.35 (s, C—NH$_2$), 147.0 (d, Ar), 133.4 (d, Ar), 128.5 (s, Ar), 123.3 (d, Ar), 72.0 (t, =N—O—CH$_2$), 66.9) t, N—CH$_2$—CH$_2$—O), 55.8 (t, —O—CH$_2$—CH$_2$—N), 53.7 (t, N—CH$_2$—CH$_2$—O), 26.3 (t, N—O—CH$_2$—CH$_2$) ppm.

EXAMPLE 6
Preparation of O-(2-piperidinoethyl)-3-pyridinehydroximoyl chloride hydrochloride 20 2.6 g (10.47 mmoles) of N-(2-piperidinoethoxy)-3-pyridinecarboxamidine are added under stirring to mixture of 17 ml of distilled water and 6 ml of concentrated hydrochloric acid, cooled to 0° C. Then, 3.62 g (52.45 mmoles) of sodium nitrite dissolved in 15 ml of distilled water are dropwise added at −5° C. during 30 minutes. After adjusting the pH value to 11 by adding 2N sodium hydroxide solution, the mixture is extracted 3 times with 50 ml of chloroform each. The organic phase is washed with 30 ml of water, dried over sodium sulfate and evaporated. The evaporation residue weighing 1.38 g (49.23%) is transformed to the title hydrochloride salt, m.p.: 149–150° C. (crystallized from ether) by adding methanolic hydrogen chloride solution.

IR (KBr) $\gamma$ cm$^{-1}$: 3433, 2945, 2633, 2540, 1587, 1450, 1414, 1271, 1059, 1038, 1007, 954, 920, 822, 706. $^1$H-NMR (DMSO-d$_6$): 11.12 (broad s, 1H), 9.03 (d, 1H, J=1.5 Hz, Ar), 8.72 (dd, 1H, J$_1$=5.3 Hz, J$_2$=1.5 Hz), 8.20 (dt, J=8.7 Hz, J$_2$=J$_3$=1.5 Hz, Ar), 7.52 (dd, 1H, J$_1$=8.7 Hz, J$_2$=5.3 Hz, Ar), 4.38 (t, J=5.0 Hz, OCH$_2$), 3.48 (t, J=5.0 Hz, overlapped CH$_2$—CH$_2$—N), 3.5–3.0 (m, 4H, N—CH$_2$—CH$_2$CH$_2$), 2.0–1.6 (m, 4H, N—CH$_2$—CH$_2$CH$_2$), 1.20 (m, ax., H, N—CH$_2$CH$_2$CH$_2$) ppm. $^{13}$C-NMR (DMSO-d$_6$): 151.6 (d, Ar), 147.3 (d, Ar), 135.8 (s, C—Cl), 134.5 (d, Ar), 127.6 (s, Ar), 123.6 (d, Ar), 69.7 (t, OCH$_2$), 53.9 (t, CH$_2$—CH$_2$N), 52.2 (t, N—CH$_2$—CH$_2$CH$_2$), 22.0 (t, N—CH$_2$—CH$_2$CH$_2$), 20.9 (t, N—CH$_2$—CH$_2$CH$_2$) ppm. Elementar analysis for C$_{13}$H$_{18}$N$_3$OCl.HCl: calculated: C 51.33; H 6.30; N 13,81%; found: C 51.4; H 6.3; N 13.8%.

The above starting substance is prepared as follows:

After dissolving 6.45 g (47.0 mmoles) of 3-pyridinecarboxamidine in 120.4 ml of 0.83N potassium hydroxide solution in ethanol under stirring, 8.65 g (47.0 mmoles) of 1-(2-chloroethyl)piperidine hydrochloride are added under stirring, then the reaction mixture is boiled under reflux for 4 hours. The precipitated potassium chloride is filtered off, the filtrate is clarified by activated carbon and evaporated. The residue is dissolved in 100 ml of chloroform, and the organic solution is washed 3 times with 100 ml of 1N sodium hydroxide solution each, then with 50 ml of water. The organic phase is dried over sodium sulfate and evaporated. The residue is purified by column chromatography (adsorbent: recrystallized from ether to give 2.69 g (23.5%) of the aimed product, m. p.: 81–83° C. (from ether).

$^1$H-NMR (DMSO-d$_6$): 8.86 (d, 1H, J=1.5 Hz, Ar), 8.60 (dd, 1H, J$_1$=5.3 Hz, J$_2$=1.5 Hz, Ar), 7.93 (dt, 1H, J=8.7 Hz, J$_2$=J$_3$=1.5 Hz, Ar), 7.28 (dd, 1H, J$_1$=8.7 Hz, J$_2$=5.3 Hz, Ar), 5.16 (broad s, 2H, NH$_2$), 4.23 (t, 2H, J=5.9 Hz, =N—O—CH$_2$), 2.70 (t, 2H, J=5.9 Hz, O—CH$_2$—CH$_2$—N), 2.48 (m, 4H, N—CH$_2$—CH$_2$—CH$_2$), 1.57 (m, 4H, —N—CH$_2$—CH$_2$—CH$_2$), 1.43 (m, 2H, N—CH$_2$—CH$_2$—CH$_2$) ppm. $^{13}$C-NMR (DMSO-d$_6$): 150.6 (d, Ar), 149.8 (s, C—NH$_2$), 147.1 (d, Ar), 133,4 (d, Ar), 128.6 (s, Ar), 123.2 (d, Ar), 71.3 (t, =N—O—CH$_2$), 54.9 (t, —O—CH$_2$—CH$_2$—N—CH$_2$), 25.8 (t, —N—CH$_2$—CH$_2$—O), 24.15 (t, —N—CH$_2$—CH$_2$—CH$_2$) ppm.

EXAMPLE 7
Preparation of O-(3-piperidinopropyl)-3-nitro-benzhydroximoyl chloride hydrochloride 3.22 g (10.5 mmoles) of N-(3-piperidinopropoxy)-3-nitrobenzamidine are added under stirring to a mixture of 15 ml of distilled water and 15 ml of concentrated hydrochloric acid, cooled to 0° C. Then, 3.62 g (52.05 mmoles) of sodium nitrite dissolved in 10 ml of water are dropwise added to the reaction mixture at −5° C. during 30 minutes. The pH value of the solution is adjusted to 10 by adding 2N sodium hydroxide solution, then it is extracted 3 times with 50 ml of chloroform each. The organic phase is washed with 30 ml of water, dried over sodium sulfate and evaporated. The evaporation residue is purified by column chromatography (adsorbent: Merck Kieselgel 60; eluent: chloroform/methanol 1:1). The obtained base, weighing 1.7 g (49.7%), is transformed to the title hydrochloride by adding an ethereal solution of hydrogen chloride, m.p.: 173–175° C.

IR (KBr) γ cm$^1$: 3420, 2926, 2953, 2649, 2546, 1614, 1591, 1533, 1452, 1354, 1295,1252, 1049, 994, 733. $^1$H-NMR (DMSO-d$_6$): 10.75 (broad s), 8.51 (t, J$_1$=J$_2$=1.9 Hz, Ar), 8.40, 8.25 (dd, 2H, J$_1$=8.1 Hz, J$_2$=1.9 Hz), 7.81 (t, J$_1$=J$_2$=8.1 Hz), 4.44 (t, J=6.2 Hz), 3.45 (m, 2H, CH$_2$NCH$_2$), 3.15 (m, 2H, CH$_2$NCH$_2$), 2.85 (m, 2H, CH$_2$—NCH$_2$), 2.25 (m, 2H, OCH$_2$CH$_2$CH$_2$N), 2.0–1.6 (m, 5H), 1.4 (m, 1H, N—CH$_2$CH$_2$CH$_2$CH$_2$CH$_2$) ppm. $^{13}$C-NMR (DMSO-d$_6$): 147.1 (s, Ar), 134.9, 132.9 (s, C—Cl), 134.9 (s, Ar), 132.7, 130.5 (d, Ar), 125.3 (d, Ar), 121.0 (d, Ar), 72.7 (t, OCH$_2$), 52.6 (t, CH$_2$—N), 51.6 (t, N—CH$_2$CH$_2$CH$_2$CH$_2$CH$_2$), 22.9, 21.2 (t, OCH$_2$CH$_2$), 22.9, 21.2 (t, N—CH$_2$CH$_2$CH$_2$CH$_2$CH$_2$ and OCH$_2$—CH$_2$), 22.0 (t, N—CH$_2$CH$_2$CH$_2$CH$_2$CH$_2$) ppm.

EXAMPLE 8
Preparation of N-[3-(1-piperidinyl)propoxy]-3'-(trifluoromethyl)benzimidoyl chloride hydrochloride To a solution containing 4 g (11.0 mmoles) of N-[3-(1-piperidinyl)propoxy]-3'-(trifluoromethyl)benzamidine hydrochloride in mixture of 10 ml of distilled water and 10 ml of concentrated hydrochloric acid, 2.07 ml of 40% aqueous sodium nitrite solution are dropwise added at a temperature of −5° C. under stirring. The reaction mixture is stirred at −5° C. and then 3 times an additional amount 1 ml of the above sodium nitrite solution each is added every 2 hours. After additional stirring for 4 hours, the excess of the reagent is decomposed with urea, then the solution is diluted with 35 ml of water and extracted twice with 35 ml of ether each. The aqueous phase is alkalinized by adding 4N sodium hydroxide solution and extracted 3 times with 40 ml of ethyl acetate each. The organic phase is washed 3 times with 20 ml of water each, 4 times with 30 ml of buffer solution (pH=5) each, then washed with 20 ml of saturated saline solution, dried over sodium sulfate and evaporated. The residue is transformed by adding a methanolic solution of hydrogen chloride to obtain the title compound in a yield of 2.56 g (60%), m.p.: 124–129° C. (from ethyl acetate).

IR (KBr) γ cm$^{-1}$: 3425 (broad), 2941, 2648, 2548, 1333, 1244, 1165, 1123, 1072, 995, 984, 802, 709, 698. $^1$H-NMR (DMSO-d$_6$): 11.0 (1H, broad, NH), 8.13 (1H, d, J=8.0 Hz), 8.05 (1H, s), 7.92 (d, 1H, J=8 Hz), 7,76 (t, 1H, J–8 Hz), Ar), 4.40 (t, 2H, J=6 Hz), OCH$_2$), 3.50–3.35 (m, 2H), 3.2–3.0 (m, 2H), 2.95–2.75 (m, 2H, 3×NCH$_2$), 2.35–2.15 (m, 2H, CH$_2$), 2.0–1.6 (m, 5H), 1.5–1.25 (m, 1H, 3×CH$_2$/piperidine) ppm. $^{13}$C-NMR (DMSO-d$_6$): 135.4 [C(Cl)=NO], 132.5, 130.7, 130.1, 129.4 (q, J=32 Hz), 127.4 (q, J=3.5 Hz), 122.8 (q, J=3,8 Hz, Ar), 123.5 (q, J=270,8 Hz, CF3), 72.6 (OCH$_2$), 52.7, 51.6 (2×NCH$_2$), 22.9, 22.0, 21.2 (3×CH$_2$) ppm. Elementar analysis for C$_{16}$H$_{20}$N$_2$OF$_3$Cl. HCl: calculated: C 49.88; H 5.49; N 7.27%; found: C 49.8; H 5.6; N 7.6%.

The above starting substance can be prepared as follows:

A solution containing 8.0 g (40 mmoles) of 3-(trifluoromethyl)benzamidoxime, 4.68 g (29.0 mmoles) of N-(3-chloropropyl)piperidine and 1.68 g (29.8 mmoles) of potassium hydroxide in 100 ml of ethanol is boiled under reflux for 2.5 hours. After filtering off the potassium chloride precipitated, the filtrate is evaporated to dryness under reduced pressure. The residue is recrystallized from water, filtered, washed with water and dried. The crude base obtained in a yield of 11.1 g (86%), m.p.: 53–62° C., is dissolved in 22 ml of ethyl acetate and acidified with 7.8 ml of 4.3 molar methanolic hydrogen chloride solution. After evaporation, the product is recrystallized from pure ethyl acetate to give 6.1 g (42.5%) of the aimed product.

(IR KBr) γ cm$^{-1}$: 3412, 3082(broad), 2949, 1655, 1325, 1171, 1121, 1072, 986, 920, 905, 808, 700. $^1$H-NMR (DMSO-d$_6$): 8.00 (s, 1H), 7.98 (d, 1H, J=8.0 Hz), 7,75 (d, 1H, J=8.0 Hz), 7.62 (t, 1H, J=8.0 Hz, Ar), 6.23 (s, 2H, NH$_2$), 3.98 (t, 2H, J=6 Hz, OCH$_2$), 2.45–2.25 (m, 6H, 3×NCH$_2$), 1.79 (quintet, 2H, J=7 Hz, CH$_2$), 1.6–1.3 (m, 6H, 3×CH$_2$/piperidine) ppm. $^{13}$C-NMR (DMSO-d$_6$): 149.6 [C(NH$_2$)=NO], 133.4, 129.5, 129.1, 128.8 (q, J=32 Hz), 125.5 (q, J=3.5 Hz) and 121.9 (q, J=3.8 Hz, Ar), 123.9 (q, J=270.8 Hz, CF$_3$), 70.8 (OCH$_2$), 55.1, 53.8 (2×nCH$_2$), 26.0, 25.3, 23.9 (3×CH$_2$) ppm. Elementar analysis for C$_{16}$H$_{22}$N$_3$OF$_3$. HCl: calculated: C 52.53; H 6.34; N 11.49%; found: C52.1; H6.3; N11.2%.

EXAMPLE 9
Preparation of N-[3-(4-methylpiperazin-1-yl)-1-propoxy]-3-pyridinecarboximidoyl chloride trihydrochloride 1.5 g (5.4 mmoles) of N-[3-(4-methylpiperazin-1-yl)-1-propoxy]-3-pyridinecarboxamidine are added under stirring to a mixture containing 10 ml of distilled water and 10 ml of concentrated hydrochloric acid, cooled to 0° C. To the yellow solution, 1.86 g (0.027 moles) of sodium nitrite dissolved in 5 ml of distilled water are dropwise added at a –5° C. temperature during 30 minutes. After stirring the reaction mixture at –5° C. for 1.5 hours, the pH value of the solution is adjusted to 10 by adding 2N sodium hydroxide solution and extracted 3 times with 50 ml of chloroform each. The organic phase is washed with 30 ml of water, dried over sodium sulfate and evaporated. After dissolving the residue in ethyl acetate, the title compound is precipitated by adding ethereal hydrogen chloride solution until the pH reaches 2. The precipitate is filtered, washed with ether and recrystallized from 80 ml of ethanol after clarifying with activated carbon to obtain the title trihydrochloride in a yield of 1.0 g (45.7%).

$^1$H-NMR (DMSO-$d_6$): 9.06 (d, 1H, J=1.6 Hz, Ar), 8.80 (d, 1H, J=4.9 Hz, Ar), 8.36 (dt, 1H, $J_1$=8.2 Hz, $J_2$=$J_3$=1.6 Hz, Ar), 7.72 (dd, 1H, $J_1$=8.2 Hz, $J_2$=4.9 Hz, Ar), 4.43 (t, 2H, 7=6.3 Hz, OCH$_2$), 3.65 (broad, 8H, NCH$_2$CH$_2$), 3.3 (t, 2H, J=7.8 Hz, CH$_2$CH$_2$CH$_2$N), 2.84 (s, 3H, CH$_3$), 2.30 (m, 2H, CH$_2$CH$_2$CHl) ppm. $^{13}$C-NMR (DMSO-$d_6$): 149.0 (d, Ar), 145.01 (d, Ar), 136.9 (d, Ar), 133.9 (s, C=N), 128.7 (s, Ar) 124.7 (d, Ar), 72.4 (t, OCH$_2$), 52.4 (t, CH$_2$—N), 49.2, 47.8 (t —N—CH$_2$—CH$_2$N), 41.7 (q, N—CH$_3$), 22.9 (t, CH$_2$CH$_2$CH$_2$) ppm.

The above starting substance can be prepared as follows:
2.74 g (0.02 moles) of 3-pyridinealdoxime are added to the solution of 1.24 g (0.022 moles) of potassium hydroxide in 30 ml of ethanol. After dissolution, 3.15 g (0.02 moles) of N-methyl-N'-(3-chloropropyl)piperazine dissolved in 10 ml of ethanol are dropwise added to the reaction mixture during about 10 minutes. The mixture is boiled under reflux for 11.5 hours while stirring. The precipitated potassium chloride is filtered off, the filtrate is clarified by the means of activated carbon and a Celite® filtering aid and then evaporated in a rotavapor equipment. The residue is dissolved in 100 ml of chloroform, washed twice with 30 ml of 2N sodium hydroxide solution each, then with 30 ml of water, the organic phase is dried over sodium sulfate and evaporated. The residue is purified by column chromatography (adsorbent: Merck Kieselgel 60; eluent: a mixture of chloroform, methanol and concentrated ammonium hydroxide in a ratio of 30:5:0.2) to obtain 1.72 g (31.0%) of product.

IR (KBr) γ cm$^{-1}$: 3387, 2947, 2802, 1730, 1639, 1450, 1389, 1283, 1242, 1194, 1150, 1083, 814, 710. $^1$H-NMR (DMSO-$d_6$): 8.85 (d, 1H, J=2.0 Hz, Ar), 8.61 (dd, 1H, $J_1$=4.9 Hz, $J_2$=2.0 Hz, Ar), 7.95 (dt, 1H, $J_1$=7.7 Hz, $J_2$=$J_3$=2.0 Hz, Ar), 7.29 (dd, 1H, $J_1$=7.7 Hz, $J_2$=4.9 Hz, Ar), 5.1 (bs, 2H, NH$_2$), 4.15 (t, 2H, J=6,4 Hz, OCH$_2$), 2.5 (m, 10H, J=5.9 Hz, —OCH$_2$—CH$_2$CH$_2$, 2×NCH$_2$—CH$_2$N), 2.27 (s, 3H, (CH$_3$), 1.95 (m, 2H, —CH$_2$—CH$_2$CH$_2$) ppm. $^{13}$C-NMR (DMSO-$d_6$): 150.5 (d, Ar), 149.3 (s, C=N), 146.9 (d, Ar), 133.3 (d, Ar), 128.5 (s, Ar), 123.1 (d, Ar), 72.0 (t, OCH$_2$) 55.2 (t, OCH$_2$CH$_2$CH$_2$), 54.9 (t, 2×NCH$_2$CH$_2$N), 53.0 (t, 2×NCH$_2$CH$_2$N), 45.9 (q, N—CH$_3$), 26.5 (t, —OCH$_2$—CH$_2$CH$_2$) ppm.

EXAMPLE 10
Preparation of O-(2,2-dimethyl-3-piperidinopropyl)-3-pyridinecarbohydroximoyl chloride To a solution containing 2.23 g (7.63 mmoles) of N-(2,2-dimethyl-3-piperidinopropoxy)-3-pyridinecarboxamidine in 30 ml of a 1:1 mixture of concentrated hydrochloric acid and water, 2.63 g (38.2 mmoles) of sodium nitrite dissolved in 10 ml of water are dropwise added at 0° C. The reaction mixture is stirred at the same temperature for an additional 2 hours, then the pH value is adjusted to 12 by adding 2N sodium hydroxide solution, and the mixture is extracted twice with 30 ml of chloroform each. The organic phase is washed with 30 ml of water, dried over sodium sulfate, filtered and evaporated. The oily residue (1.83 g) is purified by column chromatography to give the title compound as a pale yellow oil in a yield of 1.62 g (68.5%).

IR (KBr) γ cm$^{-1}$: 3433, 2934, 2783, 1583, 1475, 1416, 1271, 1157, 1113, 1055, 1034, 1003, 914, 860, 806, 704. $^1$H-NMR (CDCl$_3$): 9.06 (1H, dd, $J_1$=2.4 Hz, $J_2$=1.0 Hz, pyridine 2-H), 8.61 (1H, dd, $J_1$=4.8 Hz), $J_2$=1.7 Hz, pyridine 6H), 8.08 (1H, ddd, $J_1$=8.1 Hz, $J_2$=2.4 Hz, $J_3$=1.7 Hz, pyridine 4-H), 7.30 (1H, ddd, $J_1$=8.1 Hz, $J_2$=4.8 Hz, $J_3$=1.0 Hz, pyridine 5H), 4.14 (2H, s, OCH$_2$), 2.46 (4H, t, J=4.9 Hz, piperidine), 2.18 (2H, s, CH$_2$N), 1.55 (4H, m, piperidine), 1.37 (2H, m, piperidine), 0.94 (6H, s, CH$_3$) ppm.

The above starting material is prepared as follows:
2.74 g (0.02 moles) of pyridine-3-amidoxime are added under stirring to a solution of 2.46 g (0.044 moles) of potassium hydroxide in 40 ml of abs. ethanol under stirring. After dissolution, 4.52 g (0.02 moles) of (1-(2,2-dimethyl-3-chloropropyl)-piperidine hydrochloride are portionwise added, then an additional 10 ml of ethanol, are added. After boiling the heterogeneous mixture under reflux for 11 hours, the solid precipitate is filtered off, washed with ethanol and the solution is evaporated. After adding 100 ml of chloroform to the residue, the solution is washed twice with 100 ml of 2N sodium hydroxide solution each, then 50 ml of water. The organic phase is dried over sodium sulfate, filtered and the solution obtained is evaporated. The oily brown residue is purified by column chromatography to give the pale yellow oily product in a yield of 2.23 g (38.4%).

IR (KBr) γ cm$^1$: 3323, 2935, 2866, 2785, 1637, 1477, 1393, 1157, 111, 1057, 995, 943, 814, 708. $^1$H-NMR (CDCl$_3$): 8.87 (1H, dd, $J_1$=2.2 Hz, $J_2$=0.7 Hz, pyridine 2H), 8.60 (1H, dd, $J_1$=4.8 Hz, $J_2$=1.7 Hz, pyridine6-H), 7.93 (1H, ddd, $J_1$=8.1 Hz, $J_2$=2.2 Hz, $J_3$=1.7 Hz, pyridine-4-H), 7.30 (1H, ddd, $J_1$=8.1 Hz, $J_2$=4.8 Hz, $J_3$=0.7 Hz, pyridine-5-H), 4.89 (2H, bs, NH$_2$), 391 (2H, s, OCH$_2$), 2.48 (4H, t, J=4.8 Hz, piperidine), 2.17 (2H, s, CCH$_2$N), 1.55 (4H, m, piperidine), 1.44 (2H, m, piperidine), 0.95 (6H, s, CH$_3$), ppm.

We claim:
1. A compound of formula (I)

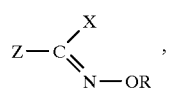

(I)

wherein:
X represents a halogen;

Z represents an aromatic group, a pyridinyl group, a picolyl group, or a lutidyl group; and R represents an —A—N(R$_1$)R$_2$ group, wherein:
R$_1$ and R$_2$ together with the adjacent nitrogen atom form a 5- to 7-membered, saturated heterocyclic group optionally containing an additional nitrogen, oxygen, or sulfur atom, said heterocyclic group optionally being substituted by at least one alkyl group; and A represents a straight or branched chain alkylene group, or a pharmaceutically acceptable acid addition salt thereof.

2. A compound of formula (I)

$$Z-C\underset{N-OR}{\overset{X}{\lessgtr}},\quad (I)$$

wherein:

X represents a halogen;

Z is selected from the group consisting of a phenyl group and a phenylalkyl group, said phenyl groups optionally substituted by 1 to 3 identical or different groups selected from the group consisting of: a halogen, a haloalkyl group, an alkyl group, a hydroxy group, an alkoxy group, a nitro group, an amino group, a monoalkylamino group, and a dialkylamino group; and R represents an —A—N(R$_1$)R$_2$ group, wherein:
R$_1$ and R$_2$ together with the adjacent nitrogen atom form a 5- to 7-membered saturated heterocyclic group optionally containing an additional nitrogen, oxygen, or sulfur atom, said heterocyclic group optionally being substituted by at least one alkyl group; and A represents a straight or branched chain alkylene group, or a pharmaceutically acceptable acid addition salt thereof.

3. A compound selected from the group consisting of:

N-(3-piperidino-1-propoxy)-3-pyridinecarboxamidine,

N-(3-morpholinopropoxy)-3-pyridinecarboxamidine,

N-(2-piperidinoethoxy)-3-pyridinecarboxamidine,

N-[3-(1-piperidinyl)-propoxy]-3'-(trifluoromethyl)benzamidine,

N-[3-(4-methylpiperazin-1-yl)1-propoxy]-3-pyridinecarboxamidine,

N-(2,2-dimethyl-3-piperidinopropoxy)-3-pyridinecarboxamidine, and the acid addition salts of these compounds.

4. A compound of formula (I)

$$Z-C\underset{N-OR}{\overset{X}{\lessgtr}},\quad (I)$$

wherein:

X represents a halogen;

Z is selected from the group consisting of a phenyl group and a phenylalkyl group, said phenyl groups optionally substituted by 1 to 3 identical or different groups selected from the group consisting of: a halogen, a haloalkyl group, an alkyl group, a hydroxy group, an alkoxy group, a nitro group, an amino group, a monoalkylamino group, and a dialkylamino group; and R represents an —A—N(R$_1$)R$_2$ group, wherein:
R$_1$ and R$_2$ represent, independently from each other, hydrogen or an alkyl group; or R$_1$ and R$_2$, together with the adjacent nitrogen atom, form a piperidino heterocyclic group, the heterocyclic group optionally being substituted by at least one alkyl group; and A represents a straight or branched chain alkylene group, or a pharmaceutically acceptable acid addition salt thereof.

5. A compound of formula (I)

$$Z-C\underset{N-OR}{\overset{X}{\lessgtr}},\quad (I)$$

wherein:

X represents a halogen;

Z represents an aromatic group, a pyridinyl group, a picolyl group, or a lutidyl group; and R represents an —A—N(R$_1$)R$_2$ group, wherein:
R$_1$ and R$_2$ represent, independently from each other, hydrogen or an alkyl group; or R$_1$ and R$_2$, together with the adjacent nitrogen atom, form a piperidino heterocyclic group, the heterocyclic group optionally being substituted by at least one alkyl group; and A represents a straight or branched chain alkylene group, or a pharmaceutically acceptable acid addition salt thereof.

6. A process for the preparation of a compound of formula (I)

$$Z-C\underset{N-OR}{\overset{X}{\lessgtr}},\quad (I)$$

wherein:

X represents a halogen;

Z represents an aromatic group, a pyridinyl group, a picolyl group, or a lutidyl group; and R represents an —A—N(R$_1$)R$_2$ group, wherein:
R$_1$ and R$_2$ represent, independently from each other, hydrogen or an alkyl group; or R$_1$ and R$_2$, together with the adjacent nitrogen atom, form a piperidino heterocyclic group, the heterocyclic group optionally being substituted by at least one alkyl group; and A represents a straight or branched chain alkylene group, or a pharmaceutically acceptable acid addition salt thereof, the process comprising:

treating a compound of formula (V)

$$Z-C\underset{\underset{H}{N}-OR,}{\overset{O}{\lessgtr}}\quad (V)$$

or a compound of formula (VI)

Z—CH=NOR, (VI)

wherein Z and R are as defined above, with a halogenating agent; and optionally, converting the obtained product prepared according to the above process to a pharmaceutically acceptable acid addition salt.

7. A process for the preparation of a compound of formula (I)

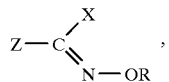
(I)

wherein:
X represents a halogen;
Z represents an aromatic group, a pyridinyl group, a picolyl group, or a lutidyl group; and
R represents an —A—N(R$_1$)R$_2$ group, wherein:
R$_1$ and R$_2$ represent, independently from each other, hydrogen or an alkyl group; or R$_1$ and R$_2$, together with the adjacent nitrogen atom, form a piperidino heterocyclic group, the heterocyclic group optionally being substituted by at least one alkyl group; and
A represents a straight or branched chain alkylene group, or a pharmaceutically acceptable acid addition salt thereof, the process comprising:
reacting a compound of formula (VII)

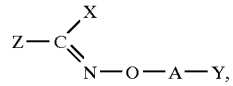
(VII)

wherein Z, X, and A are as defined above, and Y represents a leaving group, with an amine of formula HN(R$_1$)R$_2$, where R$_1$ and R$_2$ are as defined above, to obtain a compound of formula (I); and optionally, converting the obtained product prepared according to the above processes to a pharmaceutically acceptable acid addition salt.

8. A process for the preparation of a compound of formula (I)

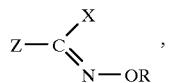
(I)

wherein:
X represents a halogen;
Z represents an aromatic group, a pyridinyl group, a picolyl group, or a lutidyl group; and
R represents an —A—N(R$_1$)R$_2$ group, wherein:
R$_1$ and R$_2$ represent, independently from each other, hydrogen or an alkyl group; or R$_1$ and R$_2$, together with the adjacent nitrogen atom, form a piperidino heterocyclic group, the heterocyclic group optionally being substituted by at least one alkyl group; and A represents a straight or branched chain alkylene group, or a pharmaceutically acceptable acid addition salt thereof, the process comprising:
a) treating a compound of formula (II)

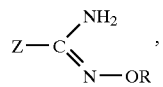
(II)

wherein Z and R are as defined above, or an acid addition salt thereof, with a diazotizing agent in the presence of a hydrogen halide, and optionally, converting the obtained product to a pharmaceutically acceptable acid addition salt.

9. A process for the preparation of a compound of formula (I) as defined in claim 2, the process comprising:
a) treating a compound of formula (II)

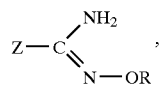
(II)

wherein Z and R are as defined above, or an acid addition salt thereof, with a diazotizing agent in the presence of a hydrogen halide; or
b) treating a compound of formula (V)

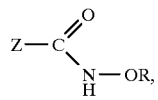
(V)

or a compound of formula (VI)

Z—CH=NOR, (VI)

wherein Z and R are as defined above, with a halogenating agent; or
c) reacting a compound of formula (VII)

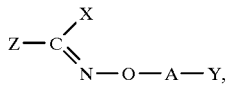
(VII)

wherein Z, X, and A are as defined above, and Y represents a leaving group, with an amine of formula HN(R$_1$)R$_2$, where R$_1$ and R$_2$ are as defined above, to obtain a compound of formula (I); and optionally, converting the obtained product prepared according to any of the above processes a), b), or c), respectively, to a pharmaceutically acceptable acid addition salt.

10. A process according to claim 9, wherein the process is process a).

11. A process according to claim 9, wherein the process is process b).

12. A process according to claim 9, wherein the process is process c).

13. A process for the preparation of a compound of formula (I) as defined in claim 4, the process comprising:

a) treating a compound of formula (II)

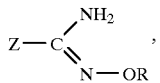  (II)

wherein Z and R are as defined above, or an acid addition salt thereof, with a diazotizing agent in the presence of a hydrogen halide; or b) treating a compound of formula (V)

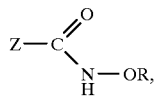  (V)

or a compound of formula (VI)

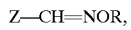  (VI)

wherein Z and R are as defined above, with a halogenating agent; or c) reacting a compound of formula (VII)

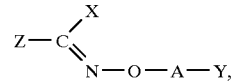  (VII)

wherein Z, X, and A are as defined above, and Y represents a leaving group, with an amine of formula $HN(R_1)R_2$, where $R_1$ and $R_2$ are as defined above, to obtain a compound of formula (I); and optionally, converting the obtained product prepared according to any of the above processes a), b), or c), respectively, to a pharmaceutically acceptable acid addition salt.

14. A process according to claim 13, wherein the process is process a).

15. A process according to claim 13, wherein the process is process b).

16. A process according to claim 13, wherein the process is process c).

17. A method of treating ischemic states or diseases in mammals, comprising: administering to said mammal a therapeutically effective amount of a compound as defined in claim 1, or a pharmaceutically acceptable acid addition salt thereof.

18. A method of treating ischemic states or diseases in mammals, comprising: administering to said mammal a therapeutically effective amount of a compound as defined in formula (I)

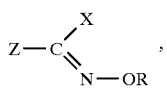  (I)

wherein:

X represents a halogen;

Z represents an aromatic group, a pyridinyl group, a picolyl group, or a lutidyl group; and R represents an $-A-N(R_1)R_2$ group, wherein:

$R_1$ and $R_2$ represent, independently from each other, hydrogen or an alkyl group; or $R_1$ and $R_2$, together with the adjacent nitrogen atom, form a piperidino heterocyclic group, the heterocyclic group optionally being substituted by at least one alkyl group; and A represents a straight or branched chain alkylene group, or a pharmaceutically acceptable acid addition salt thereof.

19. A method of treating ischemic states or diseases in mammals, comprising: administering to said mammal a therapeutically effective amount of a compound as defined in claim 2, or a pharmaceutically acceptable acid addition salt thereof.

20. A method of treating ischemic states or diseases in mammals, comprising: administering to said mammal a therapeutically effective amount of a compound as defined in claim 4, or a pharmaceutically acceptable acid addition salt thereof.

21. A method of treating ischemic states or diseases in mammals, comprising: administering to said mammal a therapeutically effective amount of a compound as defined in claim 5, or a pharmaceutically acceptable acid addition salt thereof.

* * * * *